United States Patent [19]

Dickinson

[11] 4,368,345

[45] Jan. 11, 1983

[54] CATALYST FOR DISPROPORTIONATION OF OLEFINS

[75] Inventor: Kathleen F. Dickinson, Edinburgh, Scotland

[73] Assignee: BP Chemicals Limited, London, England

[21] Appl. No.: 333,489

[22] Filed: Dec. 22, 1981

[30] Foreign Application Priority Data

Jan. 7, 1981 [GB] United Kingdom ............... 8100348

[51] Int. Cl.$^3$ .............................................. C07C 6/00
[52] U.S. Cl. .................................. 585/643; 252/465; 585/646; 585/656; 585/708
[58] Field of Search ............... 585/616, 643, 646, 656, 585/671, 708, 709, 734; 252/465

[56] References Cited

U.S. PATENT DOCUMENTS

| | | | |
|---|---|---|---|
| 3,365,513 | 1/1968 | Heckelsberg | 585/643 |
| 3,634,539 | 1/1972 | Alkema et al. | 585/643 |
| 3,786,112 | 1/1974 | Reusser et al. | 585/644 |

FOREIGN PATENT DOCUMENTS 1006049 9/1965 United Kingdom .
1266340 3/1972 United Kingdom .

*Primary Examiner*—Delbert E. Gantz
*Assistant Examiner*—A. Pal
*Attorney, Agent, or Firm*—Brooks, Haidt, Haffner & Delahunty

[57] ABSTRACT

The present invention relates to a process for the disproportionation of n-olefins comprising contacting the olefin feed with a catalyst composition comprising molybdenum oxide or tungsten oxide supported on silica. The catalyst composition is produced by impregnating a silica support with an alcoholic solution of a halide of a metal selected from molybdenum and tungsten, removing the alcoholic solvent by evaporation, and heat treating the impregnated support at an elevated temperature such that (a) the metal halide is converted to the corresponding oxide and/or an oxy-salt and (b) the halogen content thereof is reduced to less than 0.1% by weight of the total composition. By using a catalyst produced by this method, it is possible to carry out the process so as to selectively produce linear higher olefins.

10 Claims, No Drawings

CATALYST FOR DISPROPORTIONATION OF OLEFINS

The present invention relates to a process for the disproportionation of olefins.

Olefin disproportionation is a well-known process in which the feed olefin is converted to olefins of higher and lower numbers of carbon atoms. Such processes are described for example in British Pat. No. 1,006,049 in which an olefin is disproportionated over a catalyst comprising silica promoted by molybdenum oxide or tungsten oxide. In this reference the silica is impregnated with a solution of ammonium molybdate or tungstate and the silica is thereafter activated at 1,100° F. in air to produce a finished catalyst containing the metal oxide. Similarly, U.S. Pat. No. 3,786,112 describes a disproportionation conversion process in which an acyclic 1-olefin is contacted with a disproportionation catalyst comprising, amongst others, oxides of molybdenum or tungsten and an isomerisation catalyst which is a Group II metal supported on silica. The disproportionation catalyst is said to be produced by the process described in U.S. Pat. No. 3,365,513 and according to the examples in the latter, the sources of tungsten oxide and molybdenum oxide are again ammonium tungstate and ammonium molybdate respectively. The object of U.S. Pat. No. 3,786,112 is to achieve double-bond isomerisation during disproportionation and a wide spread of products is obtained including a significant amount of branched olefins.

British Pat. No. 1,208,038 discloses the use of a disproportionation catalyst prepared by impregnating a support with a solution of tungsten hexachloride in toluene. However the results indicate that little or no disproportionation was achieved with this catalyst.

It is an object of the present invention to influence the course of the disproportionation reaction in such a manner that there is a greater selectivity towards the formation of linear products, especially those having a higher number of carbon atoms compared to the feed olefin.

Accordingly, the present invention is a process for the disproportionation of n-olefins comprising contacting the olefin feed with a catalyst composition comprising molybdenum oxide or tungsten oxide supported on silica characterised in that the catalyst composition is produced by impregnating a silica support with an alcoholic solution of a halide of a metal selected from molybdenum and tungsten, removing the alcoholic solvent by evaporation, and heat treating the impregnated support at an elevated temperature such that (a) the metal halide is converted to the corresponding oxide and/or an oxy-salt and (b) the halogen content thereof is reduced to less than 0.1% by weight of the total composition.

The metal halide used as the source of tungsten is suitably a hexa-halide of tungsten, e.g. tungsten hexachloride and the source of molybdenum is suitably a molybdenum penta-halide, e.g. molybdenum pentachloride.

The impregnation solution is preferably prepared by mixing the metal halide with an alcoholic solvent of relatively low volatility e.g. a $C_1$–$C_4$ alcohol, preferably ethanol. It is believed that a reaction takes place on mixing the metal halide with the solvent leading to the formation of other metal compounds in the solution.

The silica used as support in the catalyst composition may be any conventional catalyst grade silica. For example, it may be precipitated silica gel, microspheroidal silica or flame hydrolysed silica. The silica support suitably has a surface area of at least 50 $m^2/g$, preferably between 100 and 700 $m^2/g$ and can range from fine powders to coarse granules.

The impregnation is preferably carried out by adding the solution prepared by mixing the metal halide and the solvent to the dry silica, e.g. silica gel, and agitating. If an excess of the solution is used the impregnated silica may be separated by simple decantation. Ater impregnating the silica support with a solution prepared from the metal halide, the solvent is preferably evaporated off e.g. in vacuum, prior to heat-treatment.

The heat-treatment of the impregnated silica support is suitably carried out at a temperature above 450° C., preferably between 500° and 1,500° C. The heat-treatment is preferably effected in an atmosphere containing air, oxygen or oxygenated gases to facilitate the conversion of the metal-halide to the corresponding oxide. The duration of the heat-treatment may vary from 1 second to 25 hours or more.

Catalyst compositions used for disproportionation of n-olefins and produced in this manner suitably contain between 0.5 and 40% by weight of the metal. The preferred metal contents are between 10 and 30% by weight for tungsten and between 0.5 and 5% by weight for molybdenum. It has been found that the halogen content of the final catalyst composition so produced is less than 0.1% by weight, generally less than 0.01% by weight.

The n-olefin feeds which may be disproportionated using the catalyst compositions of the present invention suitably contain between 2 and 30 carbon atoms per molecule although mixed feedstock such as polyisobutene raffinate rich in n-olefins may also be used. Thus, the preferred n-olefins feeds which may be disproportionated include ethylene, propylene, butene-1, butene-2, polyisobutene raffinate, pentene-1, pentene-2, hexene-1, hexene-2, hexene-3, heptene-1, heptene-2, heptene-3, octene-1 and octene-2.

The disproportionation of the n-olefin feed is suitably carried out by passing the n-olefin feed over the solid catalyst composition maintained at an elevated temperature, for instance a temperature above 300° C., preferably at about 400° C. The disproportionation reaction may be performed at subatmospheric, atmospheric or superatmospheric pressure. It is preferable to disproportionate the feed at pressures above 200 psig.

The liquid feed rate of the olefin per litre of catalyst is suitably between 1 and 50 l/l/hour, preferably between 3 and 20 l/l/hour.

The present invention is illustrated with reference to the following Examples in which Examples 1 to 4 illustrate the preparation of the catalysts and Examples 5 to 8 illustrate disproportionation processes according to the invention.

EXAMPLE 1

A catalyst composition containing 16% by weight of tungsten and less than 0.01% by weight of chlorine on silica was prepared as follows:

8 g of tungsten hexachloride were added to 36 ml of ethanol with stirring. When the vigorous frothing had subsided this solution was added to 75 ml of silica of pore volume 1.9 ml/g with shaking and the ethanol was removed from the resulting mixture by drying under reduced pressure for 0.75 h. The impregnated silica was then heat treated in air for 5 h at 550° C. to produce the final catalyst.

EXAMPLE 2

A catalyst composition containing 15.9% by weight of tungsten and less than 0.01% by weight of chlorine on silica was prepared as in Example 1 above by adding 5.5 g of tungsten hexachloride to 10 ml of ethanol and impregnating 37 ml of silica gel (pore volume 1.1 ml/g, meshed to 1-2.8 mm) with the resulting solution. The impregnated silica was then dried and heat treated as described in Example 1.

EXAMPLE 3

A catalyst containing 2.7% by weight of molybdenum and less than 0.01% by weight of chlorine on silica was prepared by adding 6.8 g molybdenum pentachloride to 10 ml of ethanol and impregnating 50 ml of silica with the resulting solution. The solvent ethanol was removed from the impregnated silica by drying at 90° C. under vacuum for 0.75 h and the resulting molybdenum impregnated silica was allowed to stand in distilled water for 5 min, filtered, dried under vacuum at 90° C. for 1.5 h and heat treated as in Example 1.

EXAMPLE 4

A catalyst composition containing 2.4% by weight of molybdenum and less than 0.01% by weight of chlorine on silica was prepared by adding 4 g of molybdenum pentachloride to 20 ml water and impregnating 50 ml of silica with the resulting solution. This was dried and heat treated as described in Example 1.

EXAMPLES 5-8

The catalysts prepared in Examples 1 to 4 were tested in a fixed bed tubular reactor held at 400° C. and 300 psig. The feed was butene-1 which was passed over the respective catalysts and the contact time with the catalyst was approximately 16 seconds in each case.

The results achieved are given in the Table below in which $$\% \text{ Yield} = \frac{\text{Weight of product produced}}{\text{weight of butene-1 fed}} \times 100$$

$$\% \text{ Butene conversion} = \frac{\text{butene-1 fed} - (\text{butene-1 and butene-2 in product})}{\text{butene-1 fed}} \times 100$$

$$\frac{\% \text{ selectivity to}}{\text{linear higher olefins}} = \frac{\text{total linear higher olefins}}{\text{total higher olefins not in feed}} \times 100$$

Higher olefins = olefins with Molecular weight greater than 56

| Ex No | Catalyst from | % Butene Conversion | % Yield of linear higher olefins | % Selectivity to linear higher olefins |
|---|---|---|---|---|
| 1 | Example 1 | 15 | 7.7 | 88-91 |
| 6 | Example 2 | 31 | 10.3 | 88-90 |
| 7 | Example 3 | 40 | 20.4 | 96-99 |
| 8 | Example 4 | 12 | 6.0 | 95-99 |

Comparative Tests (not prepared according to this invention)

Test 1

A catalyst composition containing 13.1% by weight of tungsten on silica was prepared as follows:

12.6 g of ammonium tungstate, $(NH_4)_{10}W_{12}O_{41}5H_2O$, were dissolved in 240 ml of water. Portions of this solution were used in successive impregnations of 50 g silica gel, removing the water under vacuum between each step. The impregnated silica was then heat-treated in air for 5 h at 550° C. to produce the final catalyst.

Test 2

A catalyst composition containing 4.9% by weight of molybdenum on silica was prepared as follows:

5.6 g of ammonium paramolybdate on silica were dissolved in 65 ml of water. This solution was used to impregnate the silica held under vacuum and the solvent was subsequently removed under vacuum. The impregnated silica was then heat treated as described in Test 1 above.

These catalysts were used for disproportionation of butene-1 as in Examples 5-8 above. The results are tabulated below.

| Catalyst from | % Butene Conversion | % Yield of linear higher olefins | % Selectivity to linear higher olefins |
|---|---|---|---|
| Test 1 | 46 | 16 | 64 |
| Test 2 | 2 | 0.4 | 62 |

EXAMPLES 9-11

Catalysts for these Examples were prepared according to the invention to contain 2.4, 3.1 and 3.8% by weight of molybdenum respectively as follows:

2.5, 3.25 and 4 g of molybdenum pentachloride were dissolved in 50 ml portions of water and each used to impregnate 100 ml of microspheroidal silica gel. The impregnated silica gels were dried under vacuum and then heat treated in air for 5 h at 550° C.

EXAMPLES 12-14

The catalysts prepared in Examples 9-11 were tested in a fixed bed tubular reactor held at 400° C. and 300 psig. The feed used was a polyisobutene plant raffinate and the contact time with the catalyst was approximately 16 seconds.

The results are given in the Table below in which the % butene conversion is now defined as follows:

$$\% \text{ butene conversion} = \frac{\text{butenes-1 and 2 fed} - \text{butenes-1 and 2 in product} \times 100}{\text{butenes-1 and 2 fed}}$$

| Ex No | Catalyst from | % Butene Conversion | % Yield of linear higher olefins | % Selectivity to linear higher olefins |
|---|---|---|---|---|
| 12 | Example 9 | 29 | 15.1 | 98 |
| 13 | Example 10 | 33 | 15.8 | 97 |
| 14 | Example 11 | 33 | 16.5 | 97 |

I claim:

1. A process for the disproportionation of n-olefins comprising contacting the olefin feed with a catalyst composition comprising molybdenum oxide or tungsten oxide supported on silica characterised in that the catalyst composition is produced by impregnating a silica support with a solution made from a halide of a metal selected from molybdenum and tungsten, removing the solvent by evaporation, and heat treating the impregnated support at an elevated temperature such that (a)

the metal is converted to the corresponding oxide and/or an oxy-salt and (b) the halogen content thereof is reduced to less than 0.1% by weight of the total composition.

2. A process according to claim 1 wherein the metal halide used as the source of tungsten is a hexa-halide of tungsten and the source of molybdenum is a molybdenum penta-halide.

3. A process according to claim 1 or 2 wherein the impregnation solution is prepared by mixing the metal halide with a solvent of relatively low volatility.

4. A process according to claim 3 wherein the solvent is water or an alcohol.

5. A process according to claim 1 wherein the silica used as support in the catalyst composition is selected from precipitated silica gel, microspheroidal silica or flame hydrolysed silica.

6. A process according to claim 1 wherein the silica support has a surface area of at least 50 $m^2/g$.

7. A process according to claim 1 wherein the heat-treatment of the impregnated silica support is carried out at a temperature above 450° C.

8. A process according to claim 7 wherein the heat-treatment is effected in an atmosphere containing air, oxygen or oxygenated gases.

9. A process according to claim 1 wherein the catalyst compositions used contain between 0.5 and 40% by weight of the metal.

10. A process according to claim 1 wherein the n-olefin feed which is disproportionated comprises a hydrocarbon containing between 2 and 30 carbon atoms per molecule and the n-olefin feed is passed over the solid catalyst composition maintained at a temperature above 300° C. and at pressures above 200 psig.

* * * * *

UNITED STATES PATENT AND TRADEMARK OFFICE
CERTIFICATE OF CORRECTION

PATENT NO. : 4,368,345
DATED : January 11, 1983
INVENTOR(S) : KATHLEEN F. DICKINSON It is certified that error appears in the above—identified patent and that said Letters Patent is hereby corrected as shown below:

Col. 3, line 58, under the heading "Ex No",
change "1" to --5--

Signed and Sealed this

Sixth Day of December 1983

[SEAL]

Attest:

GERALD J. MOSSINGHOFF

Attesting Officer     Commissioner of Patents and Trademarks